(12) United States Patent
Ahlberg et al.

(10) Patent No.: US 8,114,107 B2
(45) Date of Patent: Feb. 14, 2012

(54) LAPAROSCOPIC SCISSOR BLADES

(75) Inventors: Russell E. Ahlberg, Rancho Santa Margarita, CA (US); Charles C. Hart, Summerville, SC (US); Steven C. Kessler, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1089 days.

(21) Appl. No.: 11/735,798

(22) Filed: Apr. 16, 2007

(65) Prior Publication Data

US 2007/0244497 A1    Oct. 18, 2007

Related U.S. Application Data

(63) Continuation-in-part of application No. 10/976,505, filed on Oct. 29, 2004, now abandoned.

(60) Provisional application No. 60/517,729, filed on Nov. 5, 2003.

(51) Int. Cl.
 *A61B 17/3201* (2006.01)
(52) U.S. Cl. ...................................... 606/174
(58) Field of Classification Search ............ 30/194–197, 30/244, 254; 606/167, 170, 174, 175
 See application file for complete search history.

(56) References Cited

U.S. PATENT DOCUMENTS

| | | | |
|---|---|---|---|
| 332,657 A | 12/1885 | Humphrey | |
| 858,531 A | 7/1907 | Palmer | |
| 898,535 A | 9/1908 | Volckmann | |
| D48,202 S | 11/1915 | Smith | |
| D48,669 S | 3/1916 | Davis | |
| D56,013 S | 8/1920 | Lickert | |
| 1,474,799 A | 11/1923 | Starkey | |
| 3,834,021 A | 9/1974 | White et al. | |
| 3,883,951 A | 5/1975 | Farrell | |
| 4,856,191 A * | 8/1989 | Weber | 30/123 |
| 4,945,638 A | 8/1990 | Dietel | |
| D310,714 S | 9/1990 | Dolwick | |
| 4,970,786 A | 11/1990 | Harper | |
| 5,074,046 A | 12/1991 | Kolesky | |
| 5,312,434 A | 5/1994 | Crainich | |
| 5,352,222 A | 10/1994 | Rydell | |
| 5,392,789 A | 2/1995 | Slater et al. | |
| 5,423,842 A * | 6/1995 | Michelson | 606/167 |
| 5,478,347 A * | 12/1995 | Aranyi | 606/170 |
| 5,478,351 A | 12/1995 | Meade et al. | |
| D365,878 S | 1/1996 | Blake | |
| 5,486,189 A | 1/1996 | Mudry et al. | |

(Continued)

FOREIGN PATENT DOCUMENTS

JP    2004-24318    1/2004

(Continued)

OTHER PUBLICATIONS

Co-Pending U.S. Appl. No. 10/976,505, filed Oct. 29, 2004 Title: Multiple-Angle Scissor Blade.

(Continued)

*Primary Examiner* — Ryan Severson
(74) *Attorney, Agent, or Firm* — John F. Heal; Patrick Y. Ikehara

(57) ABSTRACT

A laparoscopic scissor with a shaft for use through an access port, such as a trocar cannula, with one or more parabolic, cubic, quadratic or higher order cutting blades extending from the shaft is provided.

21 Claims, 17 Drawing Sheets

U.S. PATENT DOCUMENTS

| | | |
|---|---|---|
| 5,522,830 A | 6/1996 | Aranyi |
| 5,569,243 A | 10/1996 | Kortenbach et al. |
| 5,573,534 A | 11/1996 | Stone |
| 5,718,714 A | 2/1998 | Livneh |
| 5,746,759 A | 5/1998 | Meade et al. |
| 5,766,166 A | 6/1998 | Hooven |
| 5,779,701 A | 7/1998 | McBrayer et al. |
| 5,827,281 A | 10/1998 | Levin |
| 5,893,875 A | 4/1999 | O'Connor et al. |
| 5,921,984 A | 7/1999 | Sutcu et al. |
| 5,928,255 A | 7/1999 | Meade et al. |
| 6,001,096 A | 12/1999 | Bissinger et al. |
| 6,024,744 A | 2/2000 | Kese et al. |
| RE36,795 E | 7/2000 | Rydell |
| 6,086,606 A | 7/2000 | Knodel et al. |
| 6,168,605 B1 | 1/2001 | Measamer et al. |
| 6,391,029 B1 | 5/2002 | Hooven et al. |
| 6,391,043 B1 | 5/2002 | Moll et al. |
| 6,447,511 B1 | 9/2002 | Slater |
| 6,464,701 B1 | 10/2002 | Hooven et al. |
| 6,558,384 B2 | 5/2003 | Mayenberger |
| 6,660,016 B2 | 12/2003 | Lindsay |
| 7,013,569 B2 | 3/2006 | Holler |
| 7,063,697 B2 | 6/2006 | Slater |
| 2003/0171747 A1 | 9/2003 | Kanehira et al. |
| 2004/0260338 A1 | 12/2004 | Kupferschmid et al. |
| 2005/0149087 A1 | 7/2005 | Ahlberg et al. |
| 2005/0192598 A1 | 9/2005 | Johnson et al. |
| 2006/0079889 A1 | 4/2006 | Scott |
| 2006/0161190 A1 | 7/2006 | Gadberry et al. |

FOREIGN PATENT DOCUMENTS

| | | |
|---|---|---|
| WO | WO 2004/039416 A2 | 5/2004 |

OTHER PUBLICATIONS

Co-Pending U.S. Appl. No. 11/059,806, filed Feb. 17, 2005 Title: System and Method for Actuating a Laparoscopic Surgical Instrument.

Co-Pending U.S. Appl. No. 11/334,027, filed Jan. 18, 2006 Title: Disposable Laparoscopic Instrument.

Co-Pending U.S. Appl. No. 11/345,964, filed Feb. 2, 2006 Title: Surgical Instrument With Removable Shaft Apparatus and Method.

* cited by examiner

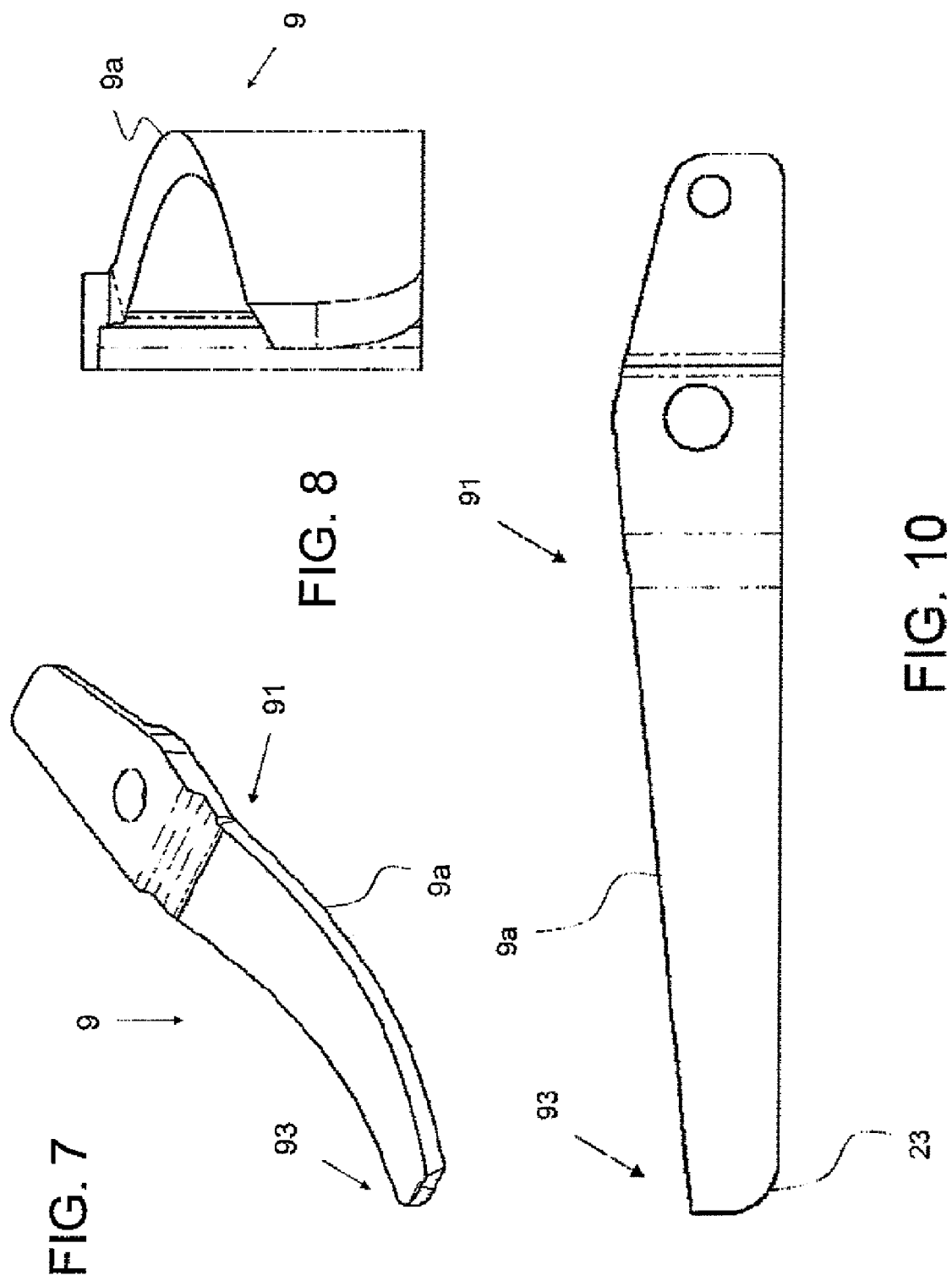

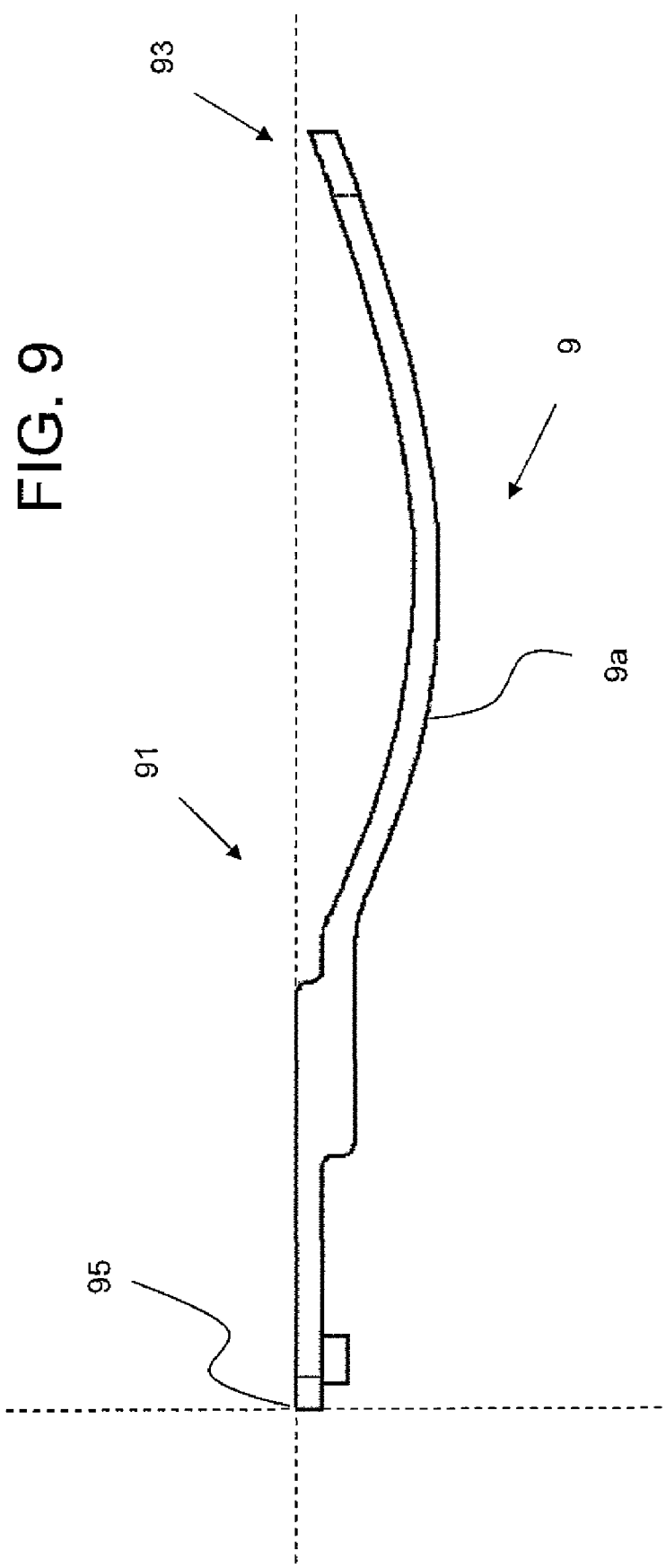

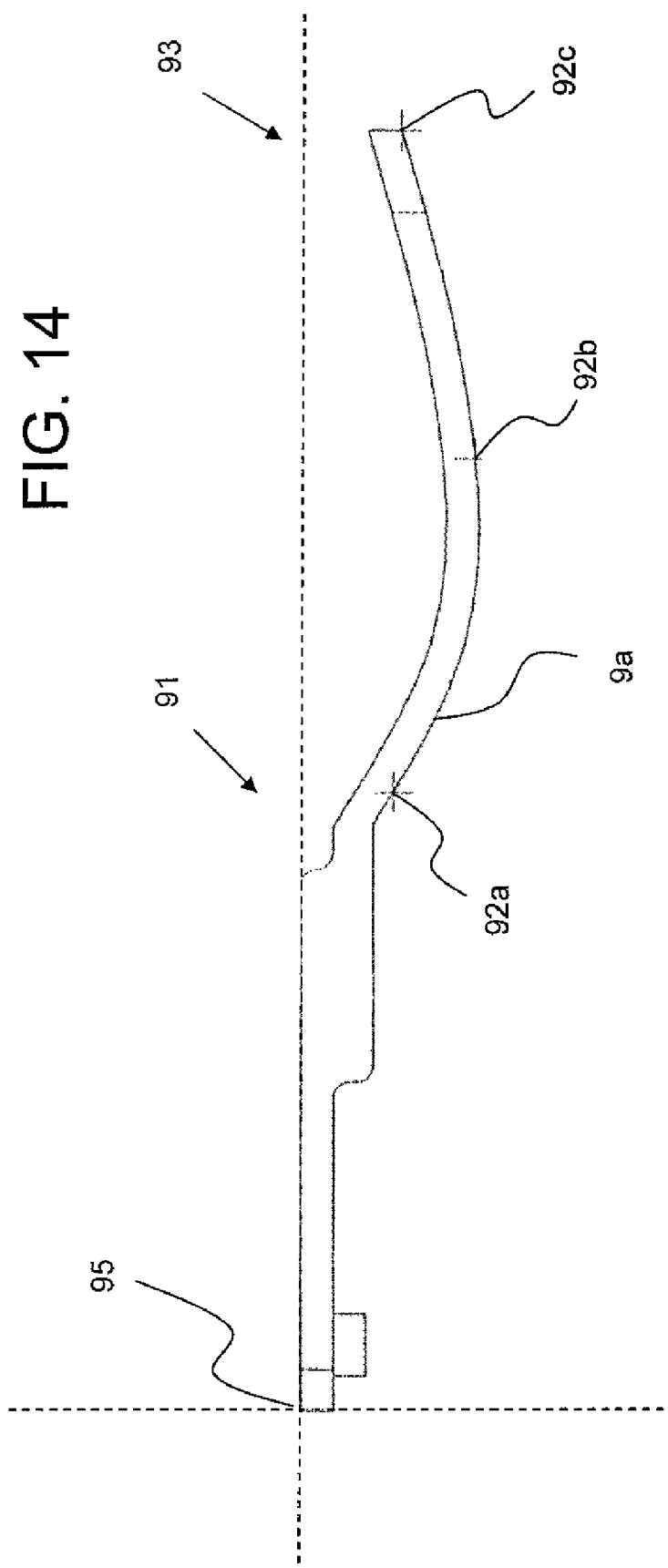

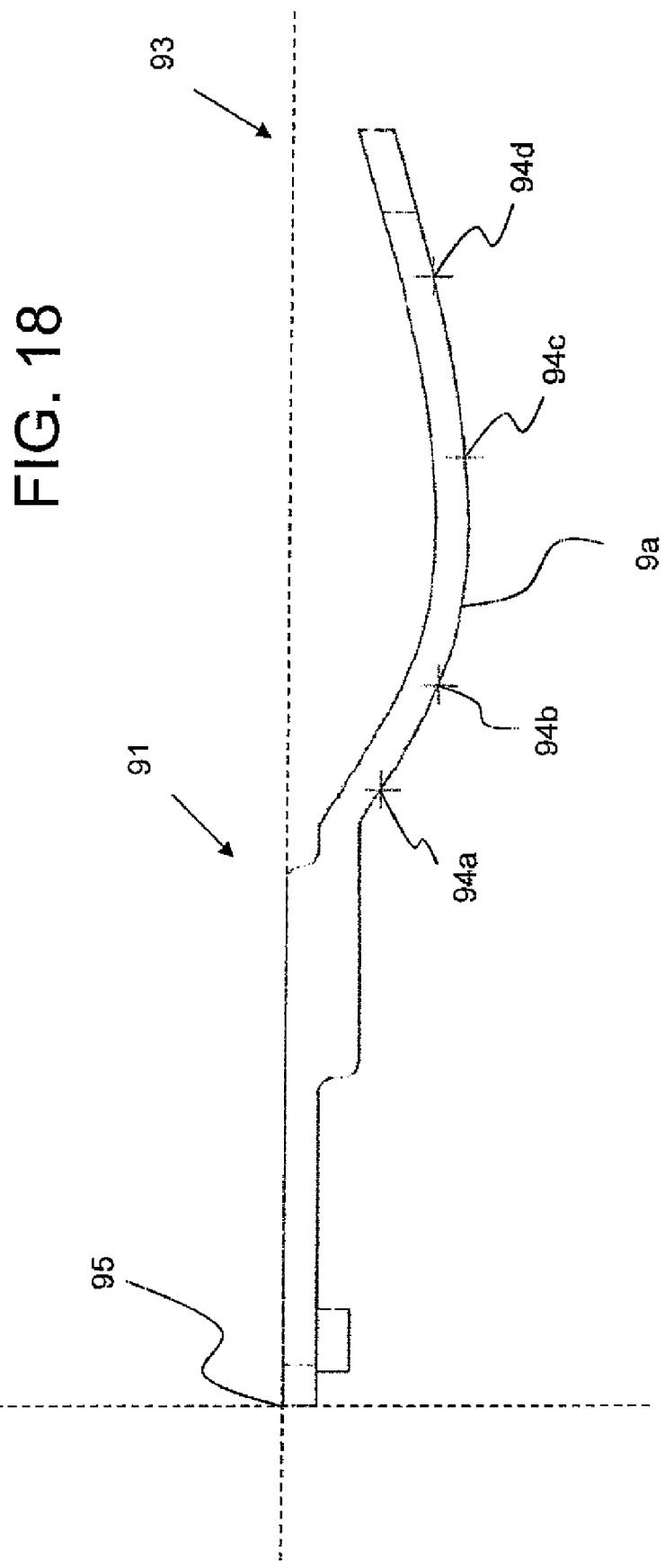

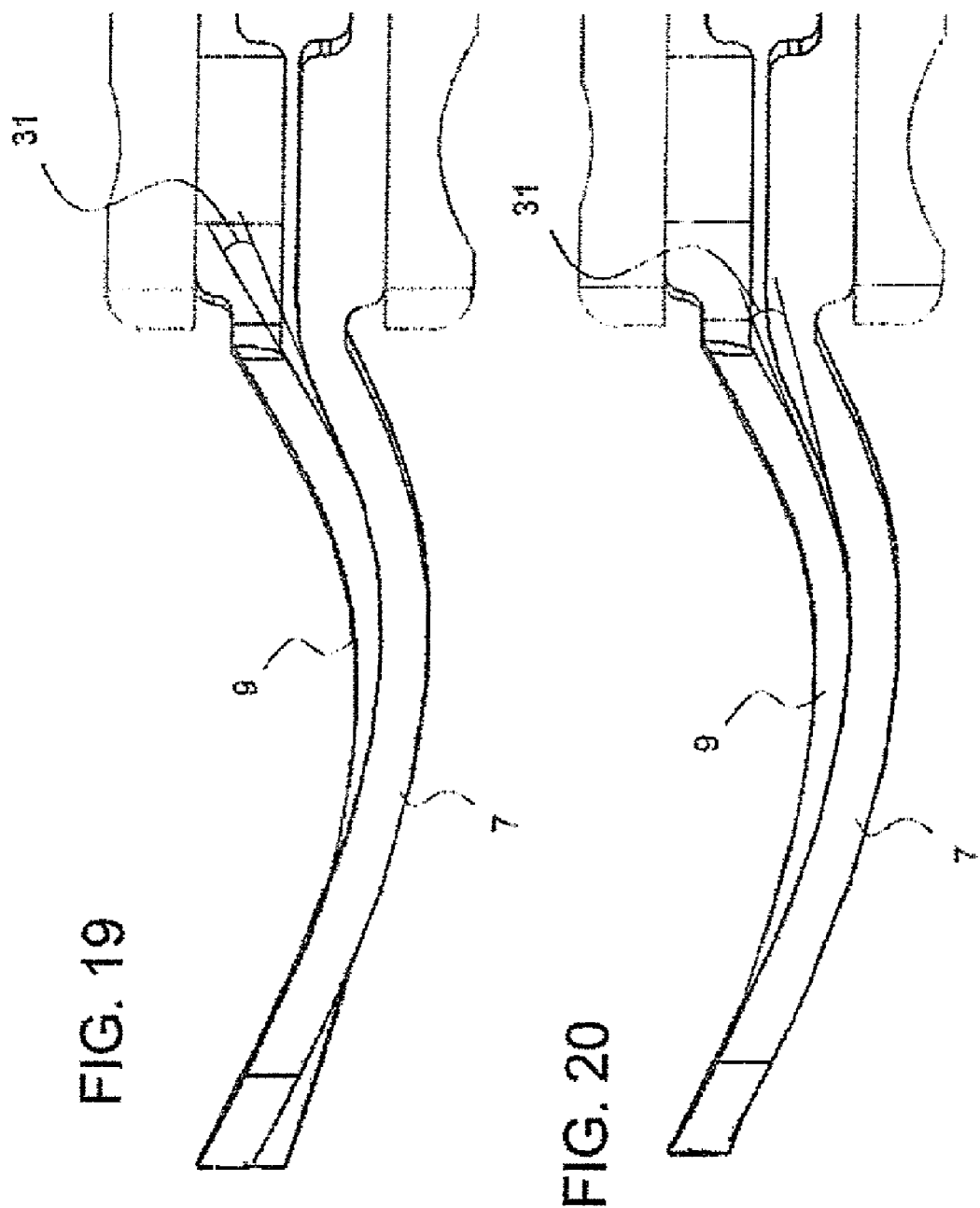

LAPAROSCOPIC SCISSOR BLADES

CROSS-REFERENCE TO RELATED APPLICATIONS

This application is a continuation-in-part of U.S. patent application Ser. No. 10/976,505, filed on Oct. 29, 2004, which claims the benefit of U.S. Provisional Application Ser. No. 60/517,729, filed on Nov. 5, 2003, the disclosures of which are hereby incorporated by reference as if set forth in full herein.

BACKGROUND

This invention generally relates to laparoscopic scissors and, more particular, to laparoscopic scissors with blades having a parabolic cutting angle.

For cutting through soft tissues, a large angle ground into the blade is most effective. That is, when sharp edges shear against each other, any tissue which comes between the blades of the scissors will get cut. The large angle on each blade is effective when cutting soft material because the blades can stay thin and razor sharp throughout the cut. A thin and sharp edge is optimal for soft materials because there is less resistance throughout the cut. However, determining and manufacturing that effective cutting edge can be difficult.

SUMMARY

In general, a laparoscopic scissor with parabolic cutting blades is provided. In one aspect, a laparoscopic scissor comprises an actuator and a shaft. The shaft is connected to the actuator and has a first and a second scissor blade extending from shaft. The first scissor blade has a first parabolic, cubic or quadratic cutting edge and a second scissor blade has a second parabolic, cubic or quadratic cutting edge.

In one aspect, a laparoscopic scissor comprises an actuator and a shaft. The shaft is connected to the actuator and has a first and a second scissor blade extending from shaft. The first scissor blade has a first parabolic cutting edge and a second scissor blade has a second parabolic cutting edge.

In one aspect, a laparoscopic scissor comprises an actuator and a shaft. The shaft is connected to the actuator and has a first and a second scissor blade extending from shaft. The first scissor blade has a first parabolic, cubic or quadratic cutting edge and a second scissor blade has a second cutting edge.

In one aspect, the first and second scissor blade edges overlap. In one aspect, the first cutting edge and the second cutting edge in contact with each other define a tension angle. The tension angle in one aspect is measured by a first tangent line extending from the first cutting edge at a contact point of the first and second cutting edges to a second line extending from the second cutting edge at the contact point of the first and second cutting edges. In one aspect, the tension angle remains constant throughout a cutting operation.

In one aspect, the first cutting edge extends from a proximal end to a distal end of the first scissor blade along a first axis. The first axis extends longitudinally along the scissor, a second axis extends perpendicular to the first axis, and a third axis is parallel to the second axis. The first and second axes intersect at a common edge point and the second and third axes intersect at an intersection point. The first cutting edge defines a shape with a first cutting point adjacent to the proximal end of the first scissor blade and has a first distance measured along the first axis from the common edge point to the intersection point. A second distance is measured along the third axis from the intersection point to the first cutting point. The second distance differs from the first distance by at least a squared order of magnitude of the first distance.

In one aspect, a second cutting edge extends from a proximal end to a distal end of the second scissor blade along a fourth axis. The fourth axis extends longitudinally along the scissor, a fifth axis extends perpendicular to the fourth axis, and a sixth axis is parallel to the fifth axis. The fourth and fifth axes intersects at a second common edge point and the fifth and sixth axes intersect at a second intersection point. The second cutting edge defines a shape with a second cutting point adjacent to the proximal end of the second scissor blade and has a third distance measured along the fourth axis from the second common edge point to the second intersection point. A fourth distance measured along the sixth axis from the second intersection point to the second cutting point. The fourth distance differs from the third distance by at least a squared order of magnitude of the third distance.

Many of the attendant features of the present invention will be more readily appreciated as the same becomes better understood by reference to the foregoing and following description and considered in connection with the accompanying drawings in which like reference symbols designate like parts throughout.

BRIEF DESCRIPTION OF THE DRAWINGS

FIG. 7 is a perspective view of a blade of a laparoscopic scissor in accordance with various aspects of the present invention;

FIG. 8 is a front view of the blade of a laparoscopic scissor in accordance with various aspects of the present invention;

FIG. 9 is a top view of the blade of a laparoscopic scissor in accordance with various aspects of the present invention;

FIG. 10 is a side view of a blade of a laparoscopic scissor in accordance with various aspects of the present invention;

FIG. 14 is a top view of the blade of a laparoscopic scissor in accordance with various aspects of the present invention;

FIG. 18 is a top view of the blade of a laparoscopic scissor in accordance with various aspects of the present invention; and FIGS. 19-22 are top views of the blades of the laparoscopic scissor during different stages of an exemplary cutting process in accordance with various aspects of the present invention.

DETAILED DESCRIPTION

Figure 1:
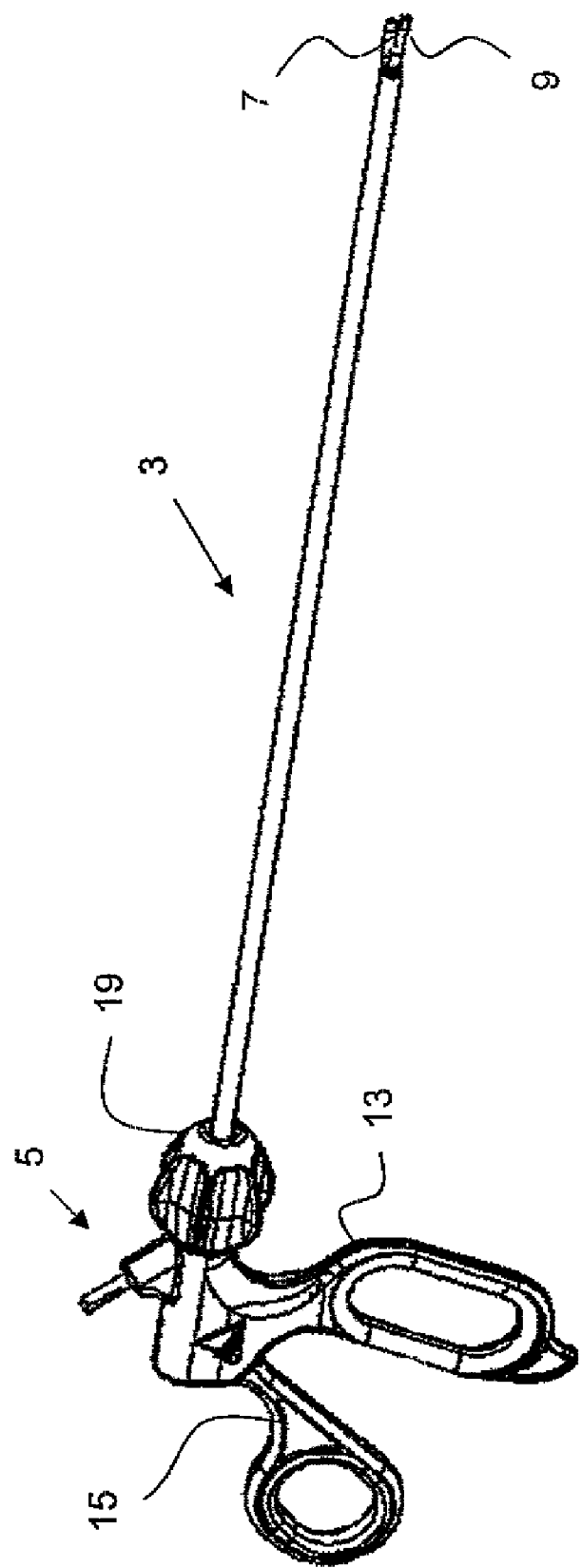
FIG. 1 is a perspective view of a laparoscopic scissor in accordance with various aspects of the present invention.
Figure 2A:
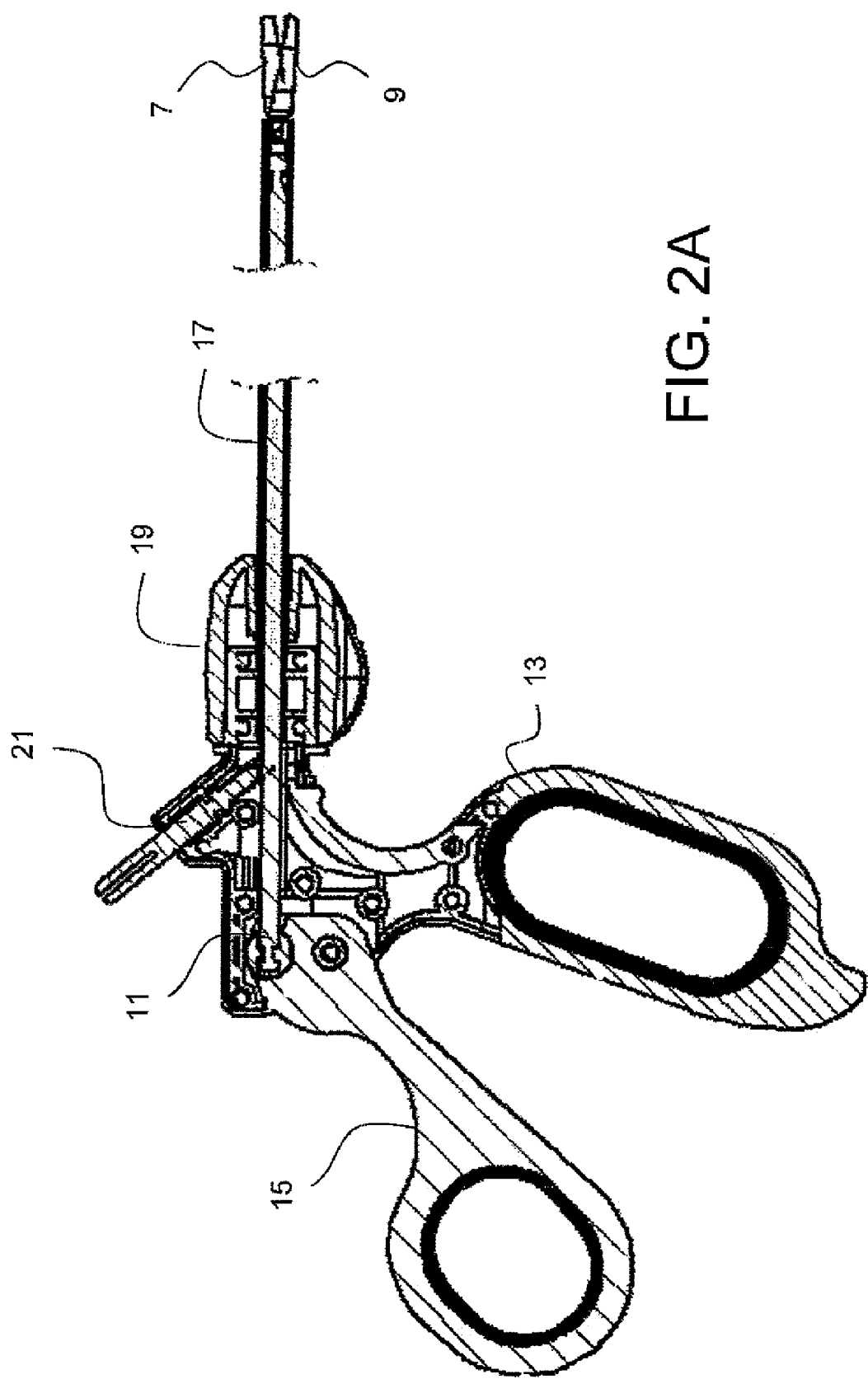
FIGS. 2A-B are cross-sectional views of a laparoscopic scissor in accordance with various aspects of the present invention.
Figure 2B:
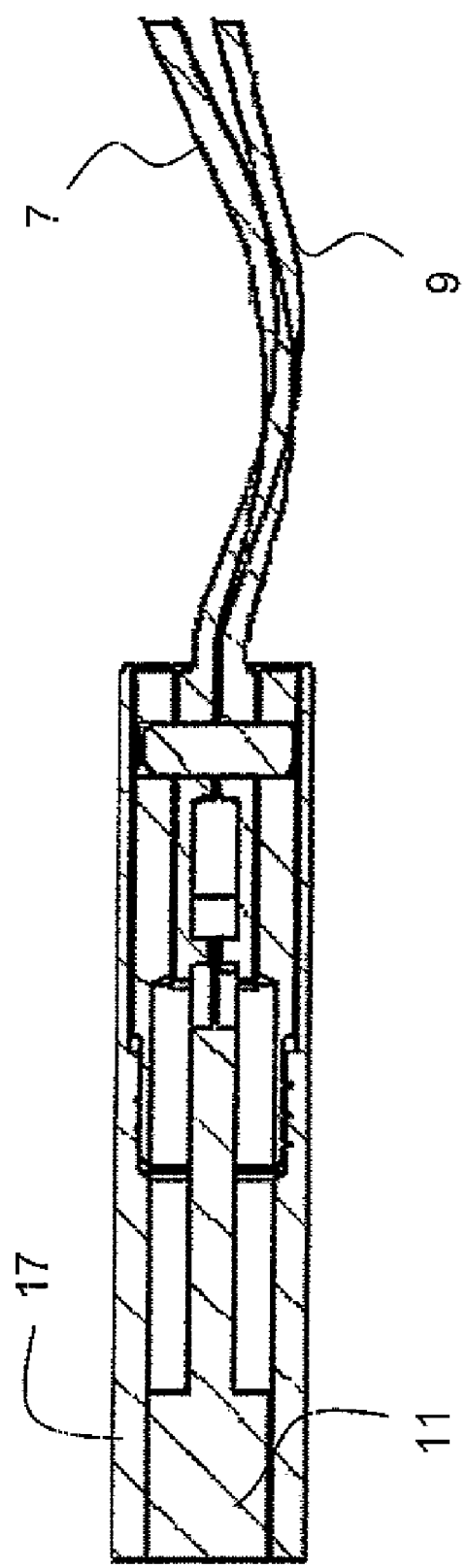
Figure 4:
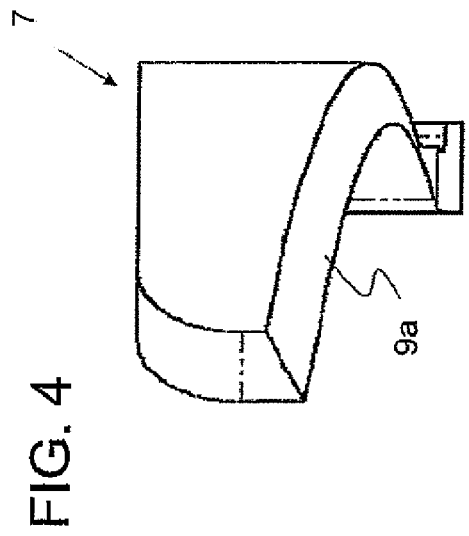
FIG. 4 is a front view of the blade of a laparoscopic scissor in accordance with various aspects of the present invention.
Figure 3:
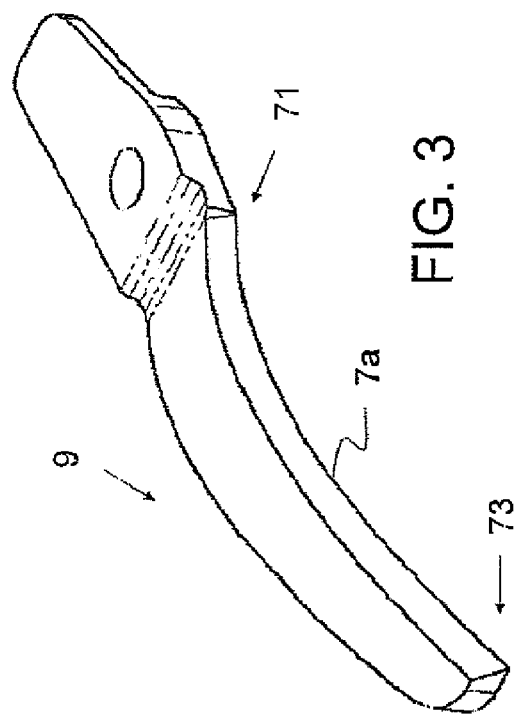
FIG. 3 is a perspective view of a blade of a laparoscopic scissor in accordance with various aspects of the present invention.
Figure 6:
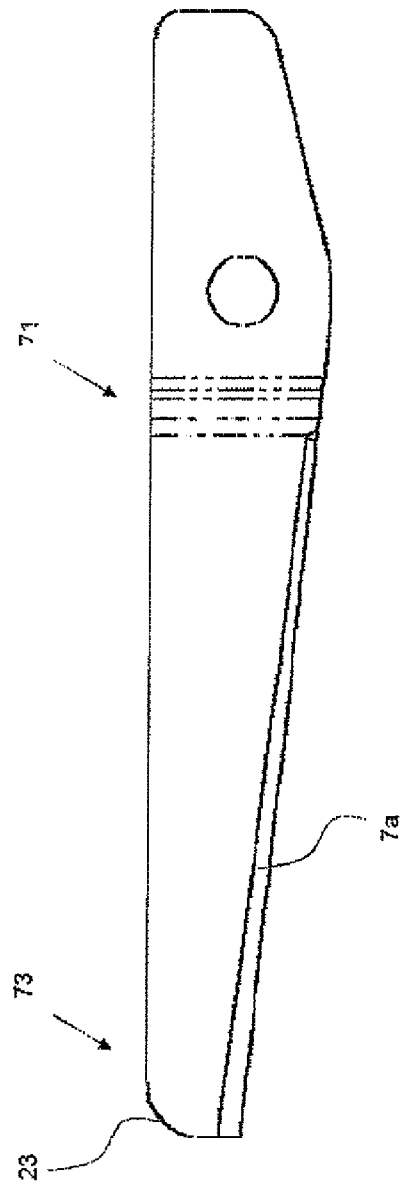
FIG. 6 is a side view of a blade of a laparoscopic scissor in accordance with various aspects of the present invention.
Figure 5:
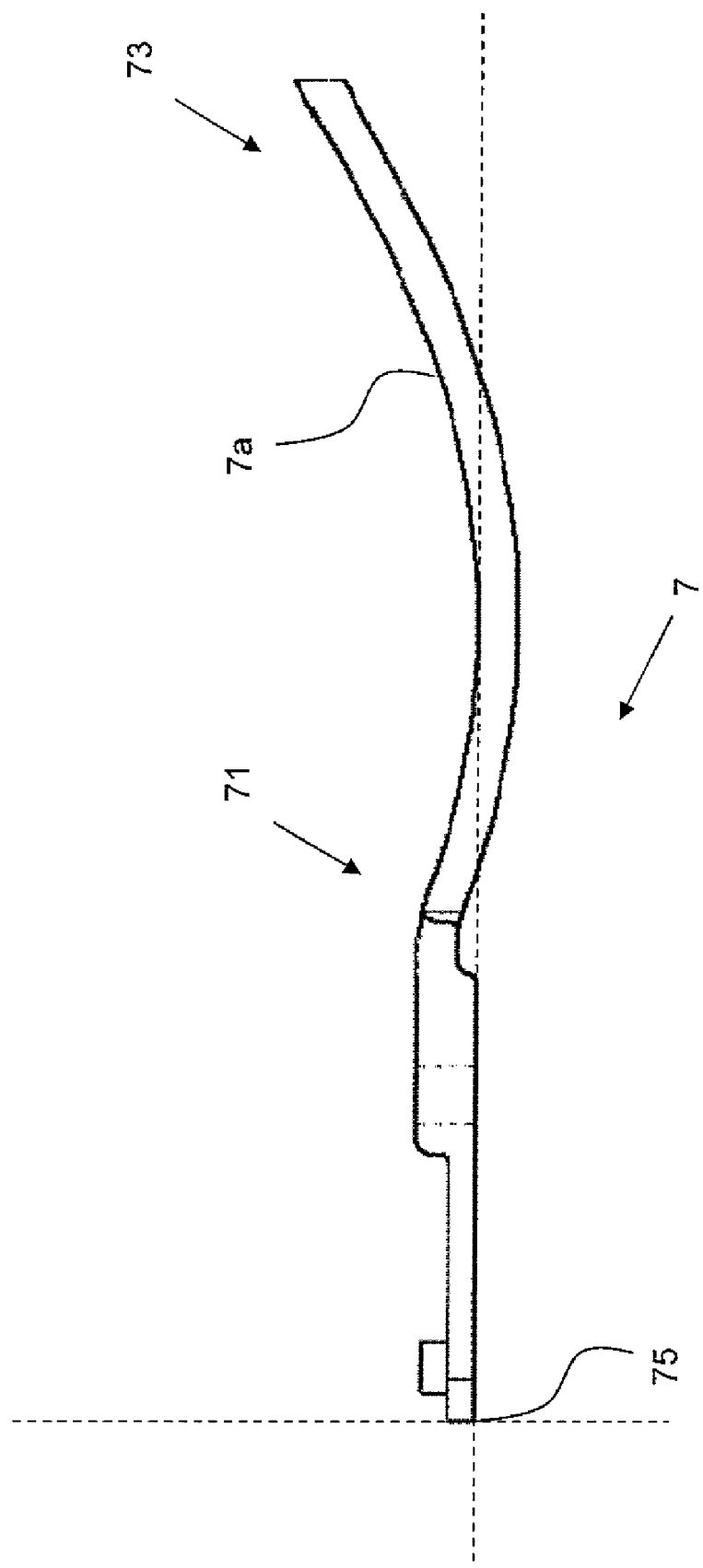
FIG. 5 is a top view of the blade of a laparoscopic scissor in accordance with various aspects of the present invention.

In FIGS. 1-2, a laparoscopic scissor is provided having a shaft 3 with a proximal end connected to an actuator 5. Extending from a distal end of the shaft 3 are scissor blades 7, 9. The shaft 3 is sized to fit through an access port, such as a trocar cannula, that extends into an insufflated abdominal cavity. As such, the shaft has a diameter of about 5 mm, but can be as much as 15 mm if desired. Extending through the shaft 3 is an actuator rod 11. The actuator rod 11 is connected to the actuator 5. The actuator 5 has a stationary handle 13 and a movable handle 15. Through manipulation of the actuator 5, e.g., movable handle 15, the scissor blades 7, 9 open or close.

The shaft 3, in one aspect, further includes a tube 17 in which the actuator rod 11 slides coaxially within and an accessible knob 19 providing 360° rotation. In one aspect, actuator rod has a connector having an enlarged end, such as a ball, that couples with the movable handle 15, fitting into a mating groove or cavity to provide a rotatable ball-and-socket joint. The tube 17 in one aspect is formed of a plastic material and the actuation rod 11 is formed of a plastic or metallic material.

In one aspect, the scissor blades are coupled to a connector. The connector is generally cylindrical having a lumen and includes a radial hole or aperture that is perpendicular to the longitudinal axis of the connector. The aperture is arranged to accept a rivet pin or dowel pin that provides a pivot point for the blades 7, 9. The connector may be coupled or press-fit into the tube 17 and in one aspect includes a clevis. The first and second blades 7, 9 are retained within the clevis of the connector by the rivet pin.

The actuator 5 may further include a connecting post 21 to provide for cauterization of tissue during a procedure. The connecting post 21 is attached to the handle so as to extend at an angle or generally perpendicular to the actuator and may include a spring. The spring extends from the connecting post 21 into contact with the actuation rod 11 to provide electrical contact as the actuation rod rotates and/or moves axially. One such exemplary scissor is described in U.S. patent application Ser. No. 11/334,027, filed Jan. 18, 2006, the disclosure of which is hereby incorporated by reference as if set forth in full herein.

The scissor blade 7 is spaced from the scissor blade 9 in a normal or open state. Likewise, the scissor blade 7 is proximate to the scissor blade 9 in an actuated or closed state. As such, the scissor blade 7 may be considered, although not limited to, an outside or outer blade in reference opposing scissor blade 9 that may be consider, although not limited to, an inside or inner blade.

Referring now to FIGS. 3-6, the scissor blade 7 has a cutting edge 7a. The cutting edge 7a extends from a proximal portion 71 of the scissor blade 7 to a distal portion 73 of the scissor blade 7. The proximal portion 71 of the scissor blade 7 extends to a connector potion that connects the blade to the shaft 3. In one aspect, the connector portion of the blade 7 has an aperture arranged to receive a pin to connect blade to a clevis in the shaft 3. A projection also extends from the connector portion of the blade 7 to couple the blade to camming slots in the actuator rod 11.

Referring also now to FIGS. 7-10, the scissor blade 9 has a cutting edge 9a. The cutting edge 9a extends from a proximal portion 91 of the scissor blade 9 to a distal portion 93 of the scissor blade 9. The proximal portion 91 of the scissor blade 9 extends to a connector potion that connects the blade 9 to the shaft 3. In one aspect, the connector portion of the blade 9 has an aperture arranged to receive a pin to connect the blade to a clevis in the shaft 3. A projection also extends from the connector portion of the blade 7 to couple the blade to camming slots in the actuator rod 11. The cutting edge 7a and cutting edge 9a shear or cut across each other during use. The blades are made of stainless steel. In one aspect, the cutting edge 7a of scissor blade 7 follows along a shape generally defined by $y=x^n$ where $n \geq 2$. The cutting edge 9a of scissor blade 9 also follows along a shape generally defined by $y=x^n$ where $n \geq 2$. The cutting edge 7a overlaps the cutting edge 9a. As the cutting edge 7a is brought into contact with the cutting edge 9a, the point of contact or cut point progressively travels along the cutting edges from the proximal portion 71, 91 to the distal portion 73, 93 of the cutting edges 7a, 9a.

Figure 11A:
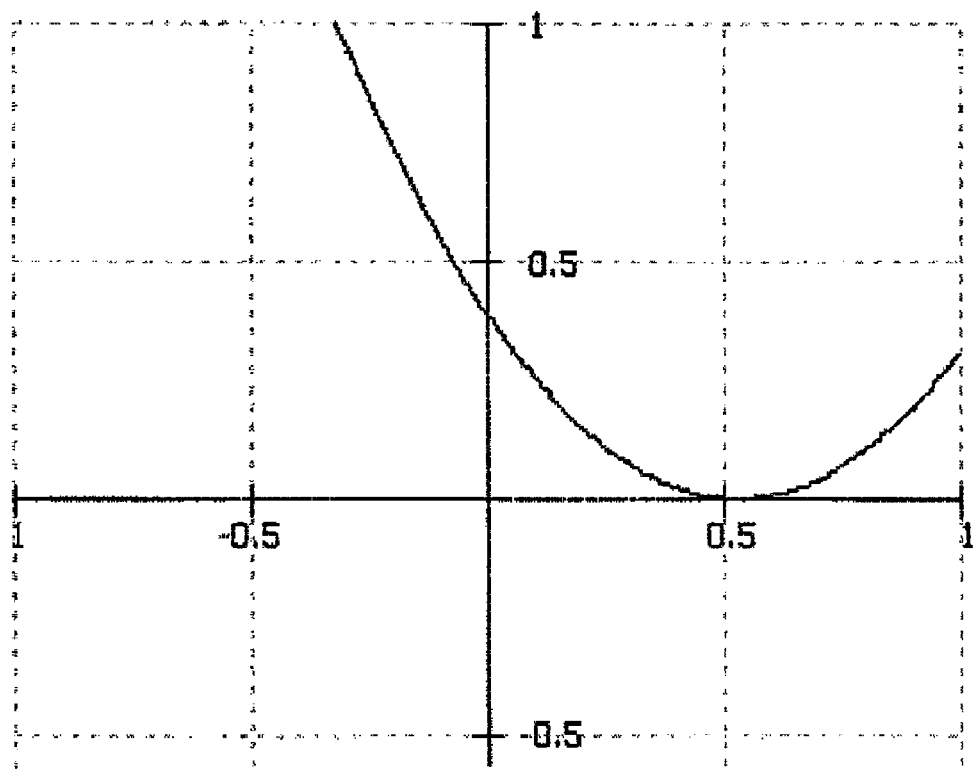
FIGS. 11A-11B are graphical representations of an exemplary shape of a cutting edge of a blade in accordance with various aspects of the present invention.
Figure 11B:
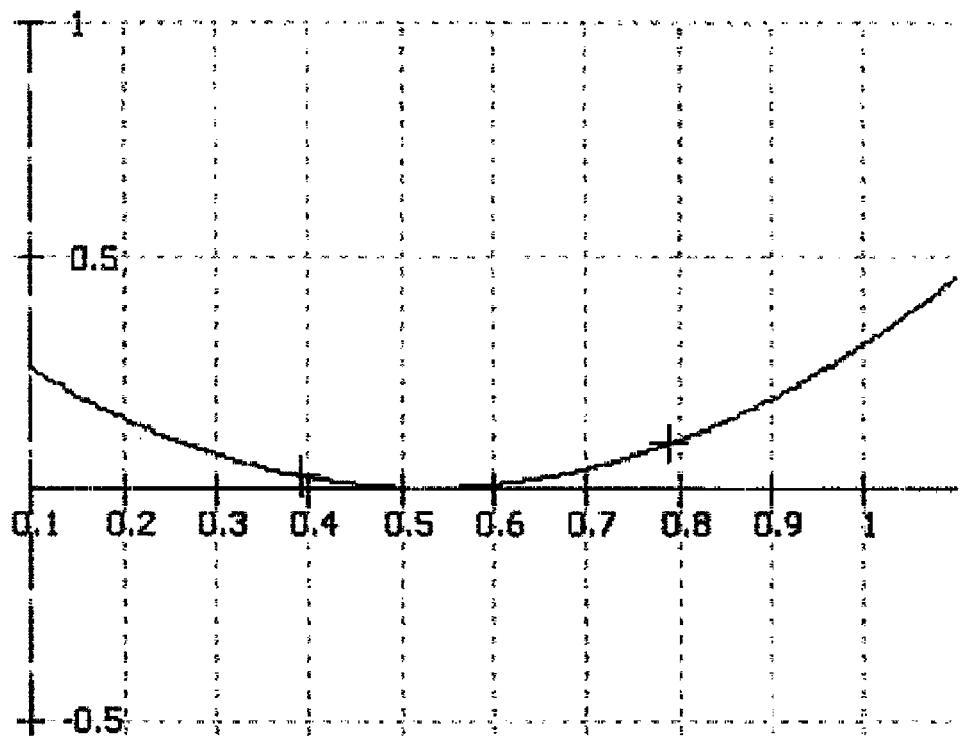
Figure 12:
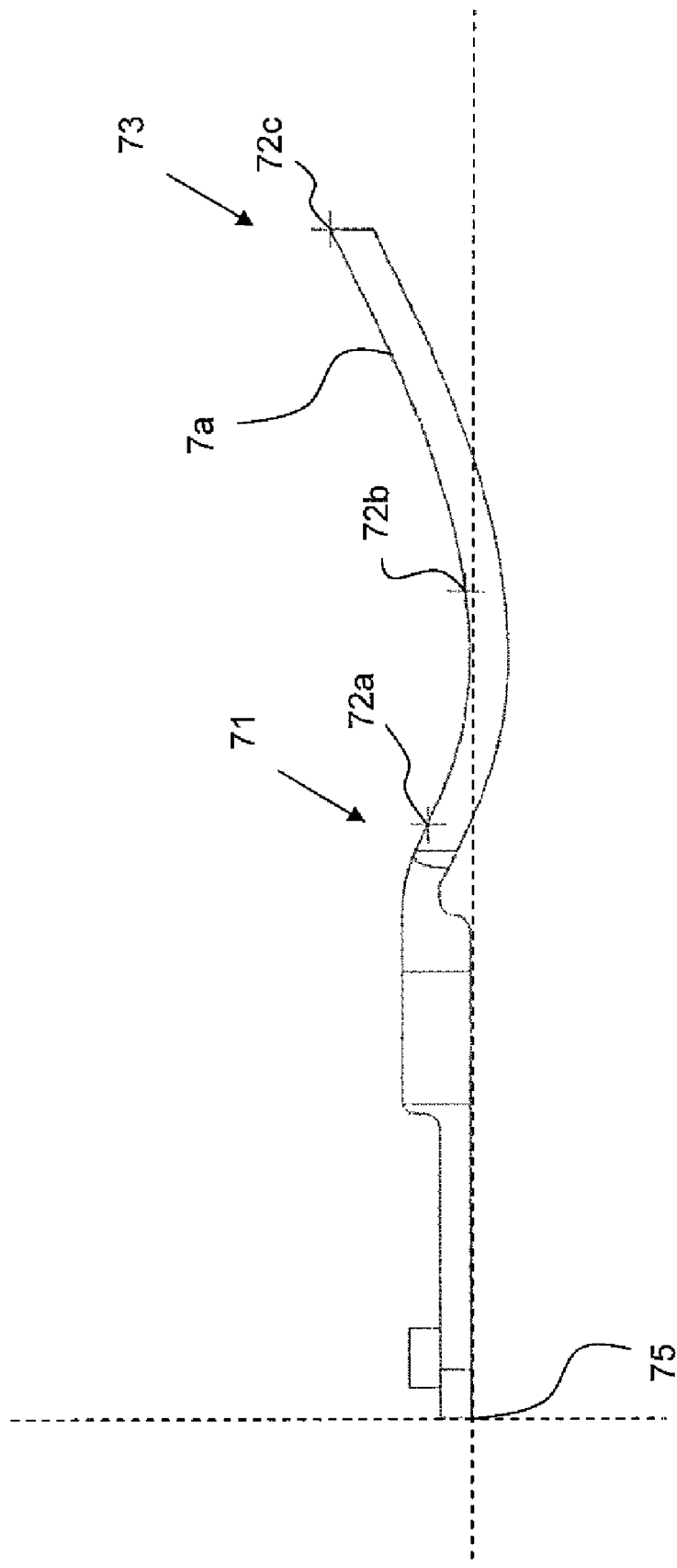
FIG. 12 is a top view of the blade of a laparoscopic scissor in accordance with various aspects of the present invention.

In one aspect, the cutting edge 7a of scissor blade 7 generally conforms to the shape defined by the expression $y=1.169x^2-1.366x+291$, where x and y parameters are measured along respective x and y axes from a common proximal end point 75 of blade 7. Graphical representations of the cutting edge 7a of scissor blade 7 following such an expression are shown in FIGS. 11A-11B. FIG. 11B is an enlarged view of the selected section for the cutting edge 7a with selected exemplary points 72a-c along the cutting edge 7a (FIG. 12) as provided in the following table.

|   | Point 72a | Point 72b | Point 72c |
|---|---|---|---|
| Y | −0.058 | −0.108 | −0.063 |
| X | 0.377 | 0.580 | 0.780 |

Figure 17A:
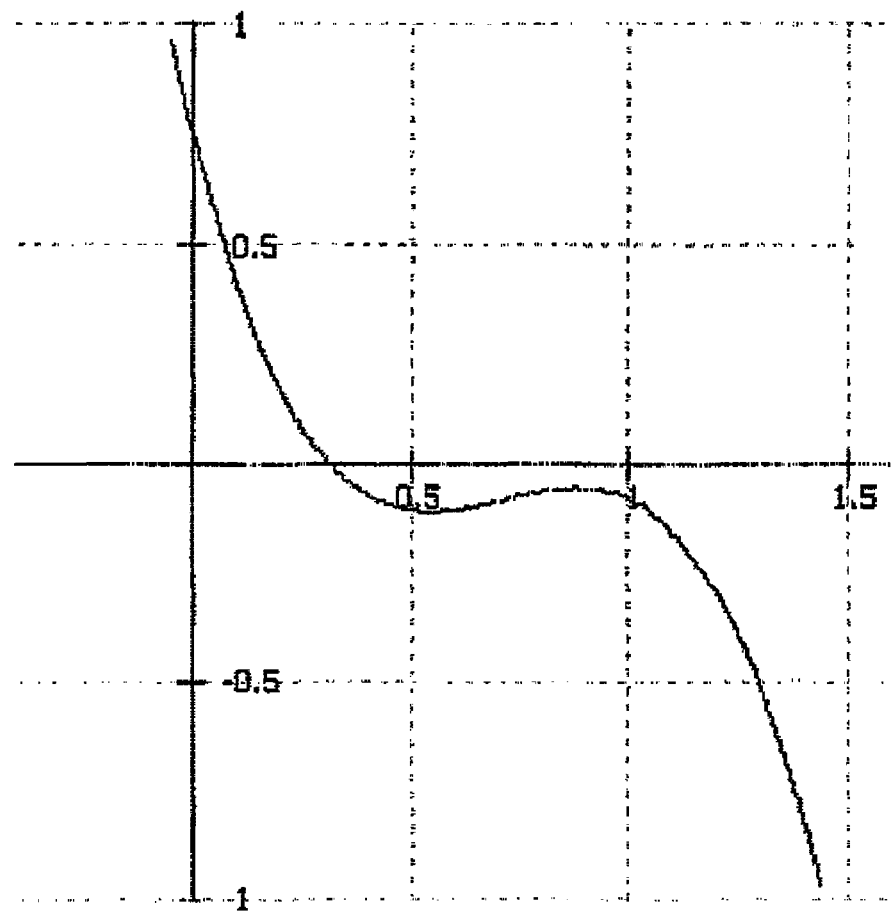
FIGS. 17A-17B are graphical representations of an exemplary shape of a cutting edge of a blade in accordance with various aspects of the present invention.
Figure 17B:
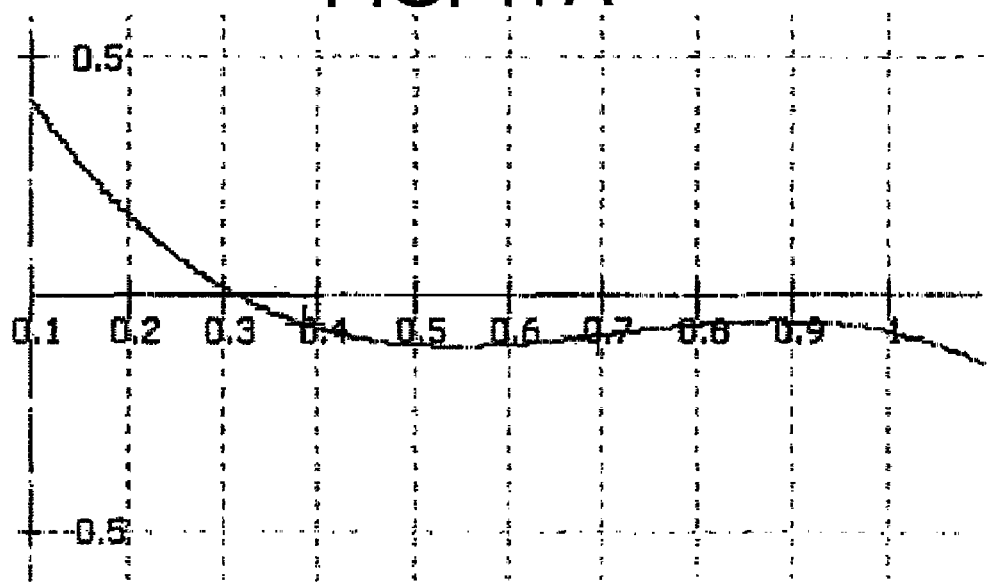
Figure 21:
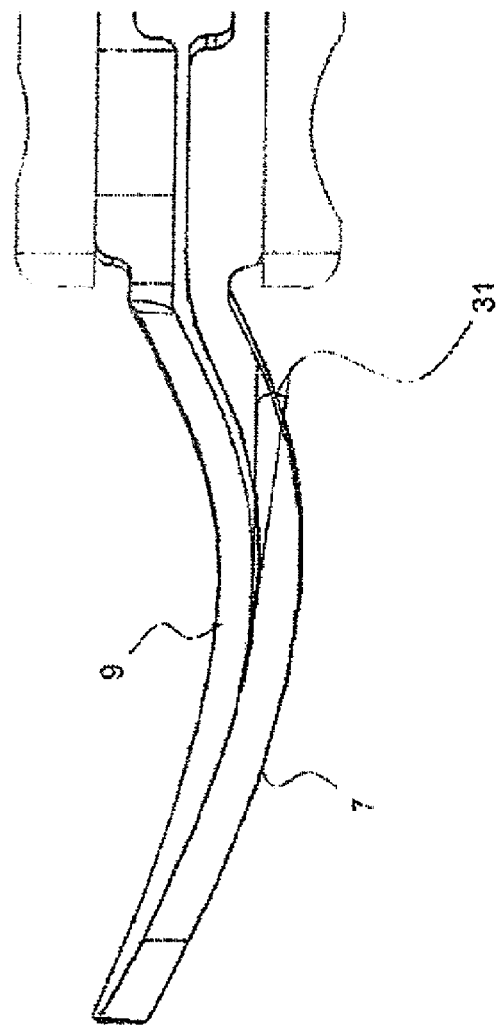
Figure 22:
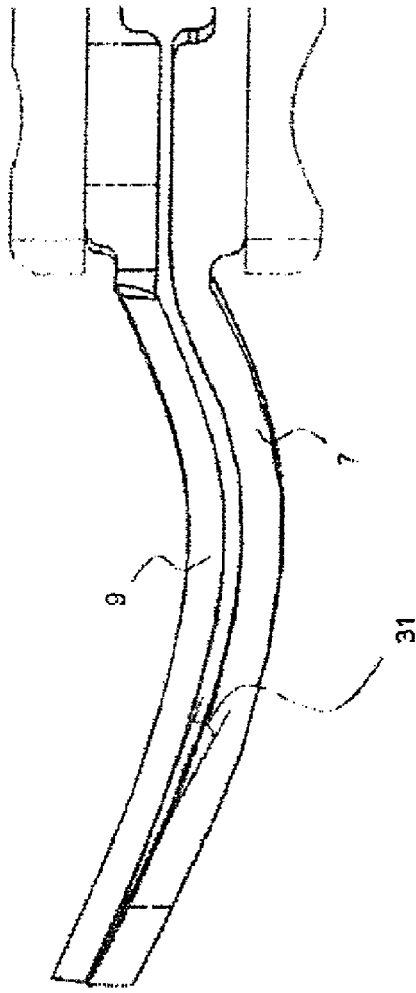

In one aspect, the cutting edge 7a generally conforms to the shape defined by the expression $y=-2.767x^3+5.918x^2-3.981x+75$, where x and y parameters are measured along respective x and y axes from a common proximal end point 75 of blade 7. Graphical representations of the cutting edge 7a of scissor blade 7 following such an expression are shown in FIGS. 17A-17B. FIG. 17B is an enlarged view of the selected section for the cutting edge 7a with selected exemplary points 74a-d along the cutting edge 7a (FIG. 18) as provided in the following table.

|   | Point 74a | Point 74b | Point 74c | Point 74d |
|---|---|---|---|---|
| Y | −0.058 | −0.092 | −0.108 | −0.088 |
| X | 0.377 | 0.441 | 0.580 | 0.691 |

Figure 13A:
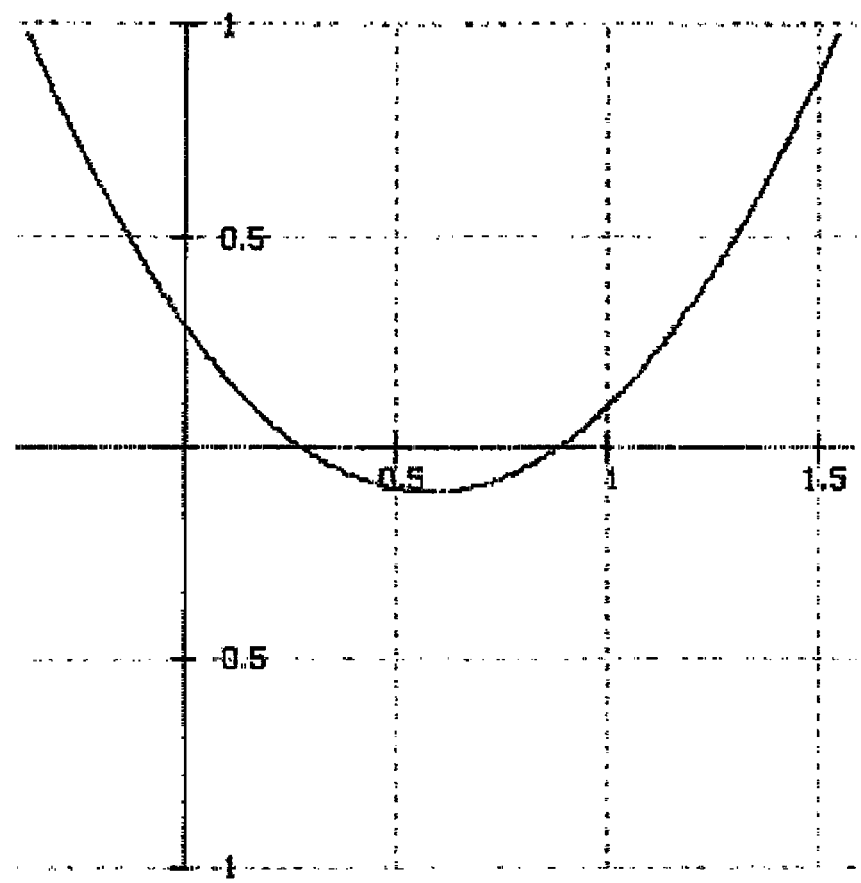
FIGS. 13A-13B are graphical representations of an exemplary shape of a cutting edge of a blade in accordance with various aspects of the present invention.
Figure 13B:
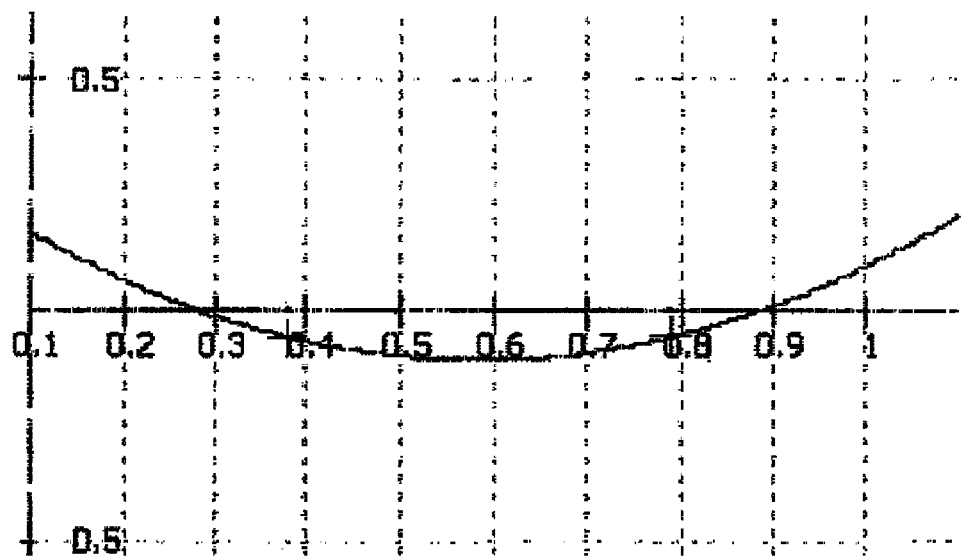

In one aspect, the cutting edge 9a of scissor blade 9 conforms to the shape defined by the expression $y=1.388x^2-1.465x+0.388$, where x and y parameters are measured along respective x and y axes from a common proximal end point 95 of blade 9. Graphical representations of the cutting edge 9a of scissor blade 9 following such an expression are shown in FIGS. 13A-13B. FIG. 13B is an enlarged view of the selected section for the cutting edge 9a with selected exemplary points 92a-c along the cutting edge 9a (FIG. 14) as provided in the following table.

|   | Point 92a | Point 92b | Point 92c |
|---|---|---|---|
| Y | 0.028 | 0.002 | 0.090 |
| Y | 0.390 | 0.543 | 0.780 |

Figure 15A:
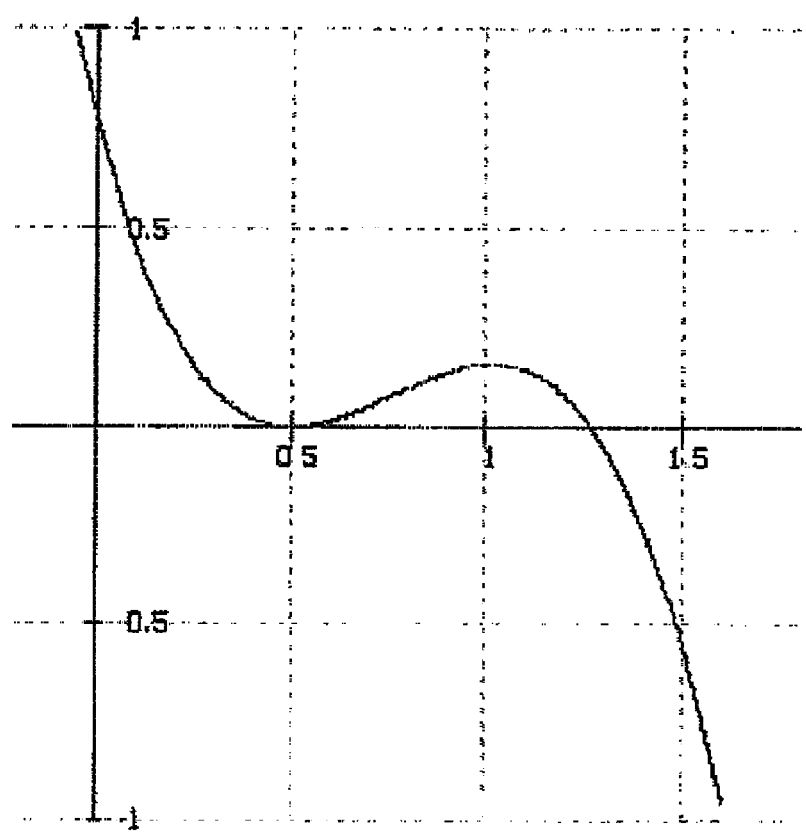
FIGS. 15A-15B are graphical representations of an exemplary shape of a cutting edge of a blade in accordance with various aspects of the present invention.
Figure 15B:
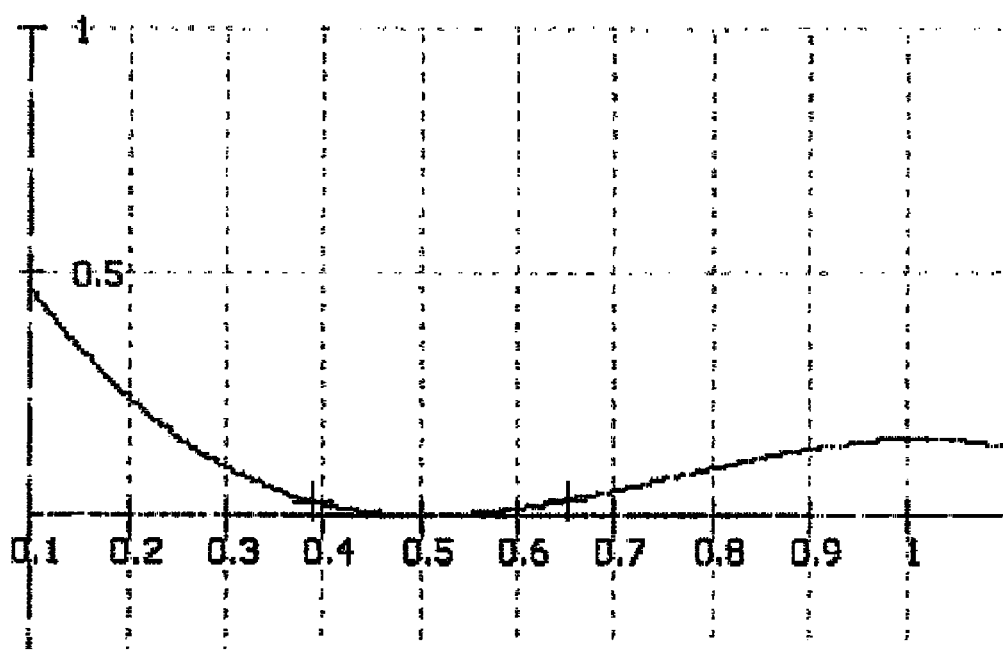
Figure 16:
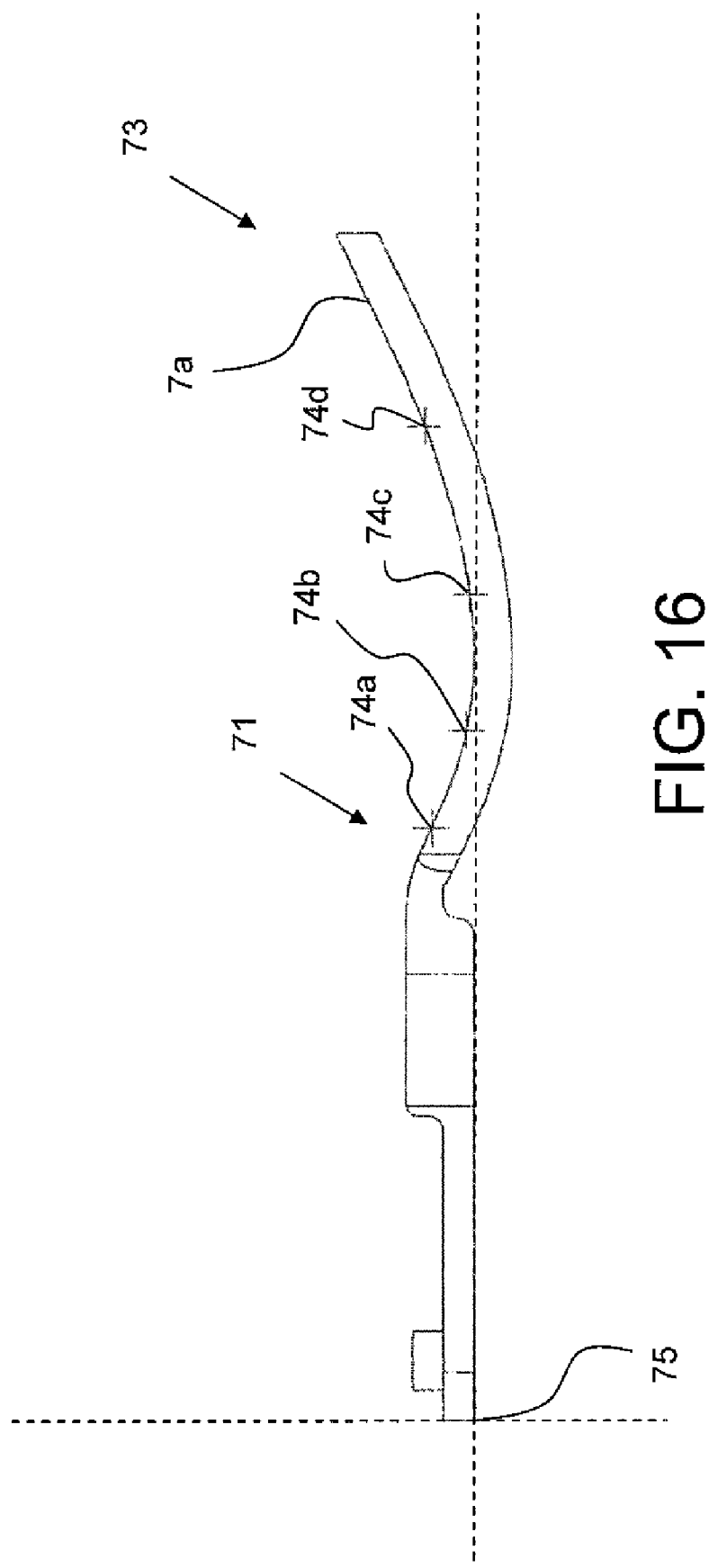
FIG. 16 is a top view of the blade of a laparoscopic scissor in accordance with various aspects of the present invention.

In one aspect, the cutting edge 9a conforms to the shape defined by the expression $y=-2.426x^3+5.53x^2-3.732x+0.786$, where x and y parameters are measured along respective x and y axes from a common proximal end point 95 of blade 9. Graphical representations of the cutting edge 9a of scissor blade 9 following such an expression are shown in FIGS. 15A-15B. FIG. 15B is an enlarged view of the selected section for the cutting edge 9a with selected exemplary points 94a-d along the cutting edge 9a (FIG. 16) as provided in the following table.

|   | Point 94a | Point 94b | Point 94c | Point 94d |
|---|---|---|---|---|
| Y | 0.028 | 0.005 | 0.002 | 0.032 |
| X | 0.390 | 0.453 | 0.543 | 0.653 |

As such, the expression and/or appropriate section on the parabolic, cubic, quadratic, or other higher order expressions of these shapes/forms can be optimized and/or selected to maximize the cutting edges 7a, 9a of each blade 7, 9 to obtain a "clean" cut.

Also, to attain a "clean" cut when the scissor blades shear across each other, it is desirable to maintain consistent tension between the blades from the apex to the tips. The tension at the apex tends to be higher than the tips because of the location of the screw or rivet holding the blade assembly together. To compensate for less tension at the tips, the blades are designed to overlap at or near the tips more than at the apex. However, having too much overlap between the blade tips can cause the cut to feel rough or abrasive because the blades are pushing rather than shearing across each other. Not enough overlap can cause the tips to cut improperly, for example, at the distal end where precise cutting is often desired.

By using blades with cutting edges in specific conforming shapes, e.g., parabolic, cubic, the blades can be adjusted so the tension between the two blades is consistent from the apex to the tip. Additionally, the overlap between the blades is constant. This results in a cut that is smooth and consistent along the entire length of the blade.

The tip or distal portion 71, 91 may also be provided by an outer edge 23. The tapered tip portion allows insertion of the scissor blades into a cavity in the body of a patient. Additionally, the tip is rounded at its outer edge to avoid inadvertent puncturing or abrasion by the tip during use.

Referring now to FIGS. 19-22, the scissor blades in various stages from open to close are shown. The angle or tension angle 31 between the blades as remains constant throughout the cutting or opening to closing or vice versa as the cut point progressively travels along the cutting edges 7a, 9a. The tension angle is measured between tangent lines extending from each blade at the cut point. That is, when the blades slide over each other during a cutting stroke, the blades flex so that only one point is actually touching. This flexure and the tension between the blades can be controlled and "forced" to different areas by maintaining the angle between the blades constant. By providing a scissors with the blades with a constant tension angle, the tension of each blade can be controlled and the flexure can be forced into certain areas on the blade, e.g., towards the tip portion of the blade.

Accordingly, the present invention provides laparoscopic scissors with parabolic, cubic, quadratic or higher order blades. Although this invention has been described in certain specific embodiments, many additional modifications and variations would be apparent to those skilled in the art. It is therefore to be understood that this invention may be practiced otherwise than specifically described, including various changes in the size, shape and materials, without departing from the scope and spirit of the present invention. For example, one of the blades may be parabolic, cubic, quadratic or higher order blades while the opposing blade is a non-higher order blade, e.g., a straight, angled or curved blade. Additionally, for example, one of the blades may be fixed or may be an extension of the shaft so that the parabolic or higher order movable cutting blade passes over the fixed cutting blade. Thus, embodiments of the present invention should be considered in all respects as illustrative and not restrictive, the scope of the present invention to be determined by the appended claims and their equivalents rather than the foregoing description.

The invention claimed is:

1. A laparoscopic scissor comprising:
    an actuator; and
    a shaft connected to the actuator and having a first and a second scissor blade extending from the shaft, the first scissor blade having a first non-planar blade surface, a first non-planar opposing surface opposite the first non-planar blade surface, the first non-planar blade surface and the first non-planar opposing surface defining one of a first parabolic, cubic and quadratic cutting edge extending between the first non-planar blade surface and the first non-planar opposing surface and the second scissor blade having a second non-planar blade surface, a second non-planar opposing surface opposite the second non-planar blade surface, the second non-planar blade surface and the second non-planar opposing surface defining one of a second parabolic, cubic and quadratic cutting edge extending between the second non-planar blade surface and the second non-planar opposing surface.

2. The scissor of claim 1 wherein the one of a first parabolic, cubic and quadratic cutting edge is different from the one of a second parabolic, cubic and quadratic cutting edge.

3. The scissor of claim 2 wherein the one of a first parabolic, cubic and quadratic cutting edge overlaps the one of a second parabolic, cubic and quadratic cutting edge.

4. The scissor of claim 2 wherein one of a first parabolic, cubic and quadratic cutting edge extends from a proximal end to a distal end of the first scissor blade along a first axis, the first axis extends longitudinally along the scissor, and a second axis extends perpendicular to the first axis, the first and second axes intersect at a common edge point and the one of a first parabolic, cubic and quadratic cutting edge defines a shape with a first cutting point adjacent to the proximal end of the first scissor blade, the first cutting point having a first distance parameter measured along the first axis from the common edge point to the first cutting point and a second distance parameter measured along the second axis from the common edge point to the first cutting point, the second distance parameter differing from the first distance parameter by at least a squared order of magnitude of the first distance parameter.

5. The scissor of claim 2 wherein one of a first parabolic, cubic and quadratic cutting edge extends from a proximal end to a distal end of the first scissor blade along a first axis, the first axis extends longitudinally along the scissor, and a second axis extends perpendicular to the first axis, the first and second axes intersect at a common edge point and the one of a first parabolic, cubic and quadratic cutting edge defines a shape with a first cutting point adjacent to the proximal end of the first scissor blade, the first cutting point having a first distance parameter measured along the first axis from the common edge point to the first cutting point and a second distance parameter measured along the second axis from the common edge point to the first cutting point, the second distance parameter differing from the first distance parameter by at least a cubed order of magnitude of the first distance parameter.

6. The scissor of claim 1 wherein the one of a first parabolic, cubic and quadratic cutting edge and the one of a second parabolic, cubic and quadratic cutting edge in contact with each other define a tension angle.

7. The scissor of claim 6 wherein the tension angle remains constant throughout a cutting operation.

8. The scissor of claim 1, wherein a curvature of the first parabolic, cubic and quadratic cutting edge is in a plane transverse to a cutting direction of the first scissor blade.

9. A laparoscopic scissor comprising:
an actuator; and
a shaft connected to the actuator and having a first and a second non-planar scissor blade extending from the shaft, the first non-planar scissor blade having a first non-planar, parabolic profile defining a first parabolic cutting edge and the second non-planar scissor blade having a second non-planar, parabolic profile defining a second parabolic cutting edge.

10. The scissor of claim 9 wherein the first parabolic cutting edge differs from the second parabolic cutting edge.

11. The scissor of claim 10 wherein the first parabolic cutting edge overlaps the second parabolic cutting edge.

12. The scissor of claim 9 wherein the first parabolic cutting edge and the second parabolic cutting edge in contact with each other define a tension angle.

13. The scissor of claim 12 wherein the tension angle remains constant throughout a cutting operation.

14. The scissor of claim 9 wherein the first parabolic cutting edge extends from a proximal end to a distal end of the first scissor blade along a first axis, the first axis extends longitudinally along the scissor, and a second axis extends perpendicular to the first axis, the first and second axes intersect at a common edge point and the first parabolic cutting edge defines a shape with a first cutting point adjacent to the proximal end of the first scissor blade, the first cutting point having a first distance parameter measured along the first axis from the common edge point to the first cutting point and a second distance parameter measured along the second axis from the common edge point to the first cutting point, the second distance parameter differing from the first distance parameter by at least a squared order of magnitude of the first distance parameter.

15. A laparoscopic scissor comprising:
an actuator; and
a shaft connected to the actuator and having a first and a second scissor blade extending from the shaft, the first scissor blade having a non-planar profile defining one of a first parabolic, cubic and quadratic cutting edge and a second scissor blade having a second cutting edge.

16. The scissor of claim 15 wherein the second cutting edge is one of a second parabolic, cubic and quadratic cutting edge being different from the one of a first parabolic, cubic and quadratic cutting edge.

17. The scissor of claim 16 wherein the one of a first parabolic, cubic and quadratic cutting edge overlaps the one of a second parabolic, cubic and quadratic cutting edge.

18. The scissor of claim 17 wherein the one of a first parabolic, cubic and quadratic cutting edge and the one of a second parabolic, cubic and quadratic cutting edge in contact with each other define a tension angle.

19. The scissor of claim 18 wherein the tension angle remains constant throughout a cutting operation.

20. The scissor of claim 19 wherein one of a first parabolic, cubic and quadratic cutting edge extends from a proximal end to a distal end of the first scissor blade along a first axis, the first axis extends longitudinally along the scissor, and a second axis extends perpendicular to the first axis, the first and second axes intersect at a common edge point and the one of a first parabolic, cubic and quadratic cutting edge defines a shape with a first cutting point adjacent to the proximal end of the first scissor blade, the first cutting point having a first distance parameter measured along the first axis from the common edge point to the first cutting point and a second distance parameter measured along the second axis from the common edge point to the first cutting point, the second distance parameter differing from the first distance parameter by at least a squared order of magnitude of the first distance parameter.

21. The scissor of claim 20 wherein one of a second parabolic, cubic and quadratic cutting edge extends from a proximal end to a distal end of the second scissor blade along a third axis, the third axis extends longitudinally along the scissor, and a fourth axis extends perpendicular to the third axis, the third and fourth axes intersect at a second common edge point and the one of a second parabolic, cubic and quadratic cutting edge defines a shape with a second cutting point adjacent to the proximal end of the second scissor blade, the second cutting point having a third distance parameter measured along the third axis from the second common edge point to the second cutting point and a fourth distance parameter measured along the fourth axis from the second common edge point to the second cutting point, the fourth distance parameter differing from the third distance parameter by at least a squared order of magnitude of the third distance parameter.

* * * * *